(12) United States Patent
Ullery et al.

(10) Patent No.: US 8,666,673 B2
(45) Date of Patent: Mar. 4, 2014

(54) IDENTIFICATION AND/OR CHARACTERIZATION OF A MICROBIAL AGENT USING TAXONOMIC HIERARCHICAL CLASSIFICATION

(75) Inventors: Michael Ullery, St. Louis, MO (US); Erin Mathias, St. Charles, MO (US); Jones M. Hyman, Wake Forest, NC (US); John D. Walsh, Durham, NC (US)

(73) Assignee: Biomerieux, Inc, Durham, NC (US)

( * ) Notice: Subject to any disclaimer, the term of this patent is extended or adjusted under 35 U.S.C. 154(b) by 637 days.

(21) Appl. No.: 12/800,379

(22) Filed: May 14, 2010

(65) Prior Publication Data

US 2011/0281291 A1 Nov. 17, 2011

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 4,118,280 A | 10/1978 | Charles et al. | 435/287.3 |
| 5,856,193 A | 1/1999 | Fanning et al. | 436/48 |
| 5,869,006 A | 2/1999 | Fanning et al. | 422/67 |
| 6,174,291 B1 | 1/2001 | McMahon et al. | 600/564 |
| 6,258,576 B1 | 7/2001 | Richards-Kortum et al. | 435/172 |
| 6,673,595 B2 | 1/2004 | Barbara-Guillem | 435/286.2 |
| 6,780,602 B2 | 8/2004 | Powers | 435/7.1 |
| 7,212,128 B2 | 5/2007 | Schenker | 340/573.1 |
| 7,991,558 B2 | 8/2011 | Kurnik | 702/19 |
| 7,991,561 B2 | 8/2011 | Kurnik | 702/19 |
| 2002/0197600 A1 | 12/2002 | Maione et al. | 435/5 |
| 2003/0170613 A1 | 9/2003 | Straus | 435/5 |
| 2005/0032115 A1 | 2/2005 | Powers et al. | 435/7.1 |
| 2005/0123917 A1 | 6/2005 | Labischinski et al. | 435/6 |
| 2005/0203709 A1* | 9/2005 | Weng | 702/19 |
| 2006/0257929 A1 | 11/2006 | Powers et al. | 435/7.1 |
| 2007/0073489 A1 | 3/2007 | Kurnik | 702/20 |
| 2007/0073490 A1 | 3/2007 | Kurnik | 702/20 |
| 2007/0105184 A1 | 5/2007 | Greenbaum et al. | 435/29 |
| 2007/0111225 A1 | 5/2007 | Lambert et al. | 435/6 |
| 2007/0143070 A1 | 6/2007 | Kurnik et al. | 702/167 |
| 2007/0143385 A1 | 6/2007 | Kurnik et al. | 702/290 |
| 2007/0148632 A1 | 6/2007 | Kurnik et al. | 435/4 |
| 2008/0032326 A1 | 2/2008 | Greenbaum et al. | 435/34 |
| 2008/0033701 A1 | 2/2008 | Kurnik | 703/2 |
| 2009/0119020 A1 | 5/2009 | Kurnik et al. | 702/19 |
| 2009/0287754 A1 | 11/2009 | Sane et al. | 708/270 |
| 2010/0068755 A1 | 3/2010 | Walsh et al. | 435/34 |
| 2010/0070190 A1 | 3/2010 | Lerner | 702/19 |
| 2011/0029252 A1 | 2/2011 | Beaty | 702/19 |
| 2011/0208432 A1 | 8/2011 | Beaty | 702/19 |

OTHER PUBLICATIONS

Michael James Bonne (Electrochemical Studies of Cellulose Matrices: Absorption, Diffusion, Reactivity and Detection, University of Bath, Department of chemistry, Sep. 2008, pp. 1-184).*
Sohn et al. (Flourescence Spectroscopy for Rapid Detection and Classification of Bacterial Pathogens, Society for Applied Spectroscopy, 2009, vol. 63, No. 11 pp. 1251-1255).*
Sanchez et al. (Spectrofluorometric Determination of Pesticide Residue Mixtures by Isodifferential Derivative Spectroscopy, 1988, American Chemical Society, pp. 323-328).*
Giana et al., J. Fluorescence 13:489-493 (2003).*
Efrima et al., *Silver Colloids Impregnating or Coating Bacteria*, Journal of Physical Chemistry B, 102(31), pp. 5947-5950, 1998.
International Search Report dated Jul. 20, 2011, in PCT/US2010/034929 filed May 14, 2010.
Udelhoven, et al., *Development of a Hierarchical Classification System with Artificial Neural Networks and FT-IR Spectra for the Identification of Bacteria*, Applied Spectroscopy, vol. 54, No. 10, pp. 1471-1479, 2000.
Wu et al., *Learning Classifiers Using Hierarchically Structured Class Taxonomies*, Zucker and Saitta Eds., SARA 2005, LNAI 3607, pp. 313-320, Springer-Verlag Berlin Heidelberg 2005.
Buck et al., *Automated, rapid identification of bacteria by pattern analysis of growth inhibition profiles obtained with Autobac 1*, J. of Clinical Microbiology, vol. 6, No. 1, pp. 46-49, 1977.
Afseth, NK et al., *Raman spectra of biological samples: A study of preprocessing methods*, Applied Spectroscopy, vol. 60, No. 12, pp. 1358-1367, Dec. 2006.
Lakowicz, *Radiative decay engineering5: metal-enhanced fluorescence and plasmon emission*, Anal. Biochem, 337, pp. 171-194, 2005.
Eisinger, J. and Flores, J., *Front-face fluorometry of liquid samples*, Anal. Biochem, 94, pp. 15-21, 1979.
Rossi, T.M, et al., "Fourier Transform Filtering of Two-Dimensional Fluorescence Data," Applied Spectroscopy, vol. 38, No. 3, pp. 422-429, 1984.
Rossi, T.M, et al., "Pattern Recognition of Two-Dimensional Fluorescence Data Using Cross-Correlation Analysis," Applied Spectroscopy, vol. 39, No. 6, pp. 949-959, 1985.
Rossi, T.M, et al., "Rank Estimation of Excitation-Emission Matrices Using Frequency Analysis of Eigenvectors," Analytical Chemistry, vol. 58, pp. 810-815, 1986.

* cited by examiner

*Primary Examiner* — Jason Sims
(74) *Attorney, Agent, or Firm* — McDonnell Boehnen Hulbert & Berghoff LLP

(57) ABSTRACT

A method for identification and/or characterization of a microbial agent present in a sample includes a step of analytical test data (e.g., obtaining intrinsic fluorescence values over a range of emission wavelengths) from the microbial agent. The analytical test data is transformed thereby minimizing strain to strain variations within an organism group. With the aid of a programmed computer, a multi-level classification algorithm coded as a set of processing instructions operates on the transformed analytic test data. The multiple levels correspond to different levels in a taxonomic hierarchy for microbial agents suspected of being in the sample.

18 Claims, 12 Drawing Sheets

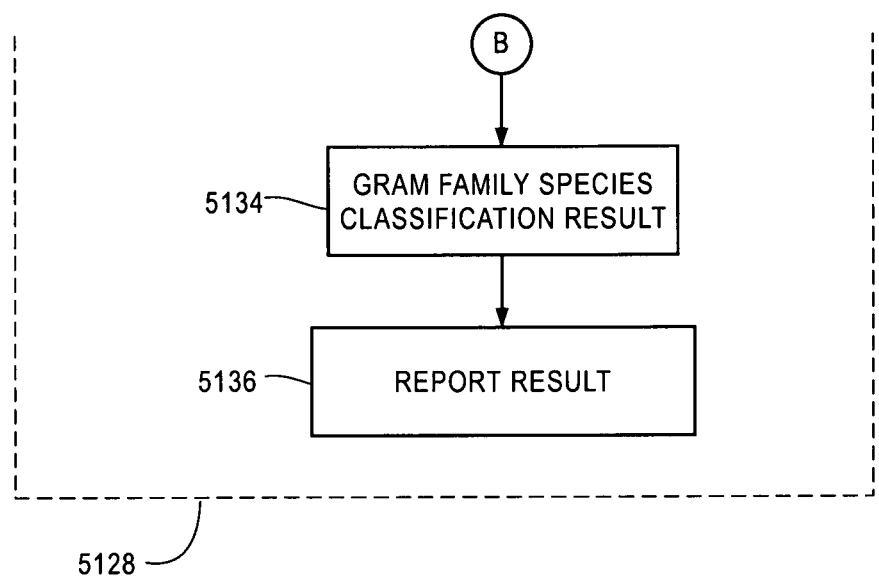

STRAIN-TO-STRAIN VARIATION IN FLUORESCENCE SIGNAL AT EXCITATION 315
AFTER APPLICATION OF THE NATURAL LOGARITHM TRANSFORMATION

STRAIN-TO-STRAIN VARIATION IN FLUORESCENCE SIGNAL AT EXCITATION 415
AFTER APPLICATION OF THE NATURAL LOGARITHM TRANSFORMATION

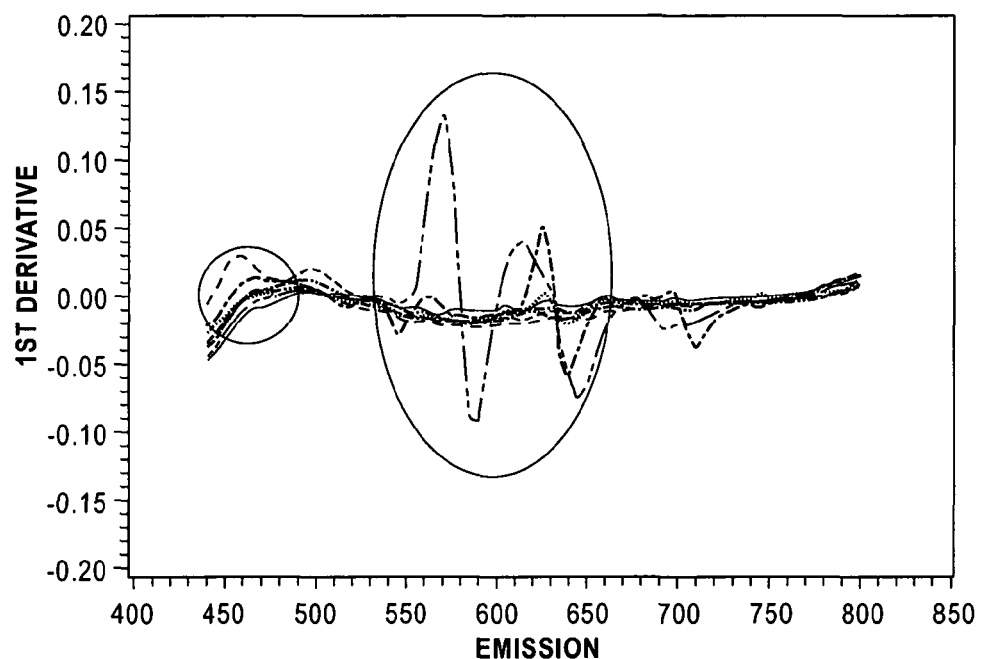

IDENTIFICATION AND/OR CHARACTERIZATION OF A MICROBIAL AGENT USING TAXONOMIC HIERARCHICAL CLASSIFICATION

CROSS-REFERENCE TO RELATED APPLICATIONS

This application is related to the following US patent applications, the content of which is incorporated by reference herein:

U.S. Ser. No. 12/589,929, entitled "Methods for the isolation and identification of microorganisms", filed Oct. 30, 2009.

U.S. Ser. No. 12/589,969, entitled "Separation device for use in the separation, identification and/or characterization of microorganisms", filed Oct. 30, 2009.

U.S. Ser. No. 12/589,952, entitled "Method for separation, identification and/or characterization of microorganisms using spectroscopy", filed Oct. 30, 2009.

U.S. Ser. No. 12/589,936, entitled "Method for separation, identification and/or characterization of microorganisms using mass spectrometry", filed Oct. 30, 2009.

U.S. Ser. No. 12/589,985, entitled "Method for separation and characterization of microorganisms using identifier agents", filed Oct. 30, 2009.

U.S. Ser. No. 12/589,968, entitled "Method for detection, identification and/or characterization of microorganisms in a sealed container", filed Oct. 30, 2009.

U.S. Ser. No. 12/589,976, entitled "Method for separation, identification and/or characterization of microorganisms using Raman spectroscopy", filed Oct. 30, 2009.

This application is also related to the following application filed on the same date as this application, the content of which is incorporated by reference herein:

"System for rapid identification and/or characterization of a microbial agent in a sample," U.S. Ser. No. 12/800,388 filed May 14, 2010.

"Methods for rapid identification and/or characterization of a microbial agent in a sample," U.S. Ser. No. 12/800,387 filed May 14, 2010.

STATEMENT OF FEDERALLY SPONSORED RESEARCH

Not applicable.

BACKGROUND

This invention relates to the field of methods for automatically characterizing and/or identifying a microbial agent present in a sample, such as blood or other biological sample, stored in a specimen container. As an example, the methods of this disclosure provides information as to Gram type (positive or negative), morphology, species or other relevant clinical information of the microbial agent rapidly and automatically.

Instruments currently exist on the market in the U.S. that detect the growth and therefore the presence of a microorganism in a blood sample. One such instrument is the BacT/ALERT 3D instrument of the present assignee bioMérieux, Inc. The instrument receives a blood culture bottle containing a blood sample, e.g., from a human patient. The instrument incubates the bottle. Periodically during incubation an optical detection unit in the incubator analyzes a colorimetric sensor incorporated into the bottle to detect whether microbial growth has occurred within the bottle. The optical detection unit, specimen containers and sensors are described in the patent literature, see U.S. Pat. Nos. 4,945,060; 5,094,955; 5,162,229; 5,164,796; 5,217,876; 5,795,773; and 5,856,175, the entire content of each of which is incorporated by reference herein. Other prior art of interest relating generally to the detection of microorganisms in a biological sample includes the following patents: U.S. Pat. No. 5,770,394, U.S. Pat. No. 5,518,923; U.S. Pat. No. 5,498,543, U.S. Pat. No. 5,432,061, U.S. Pat. No. 5,371,016, U.S. Pat. No. 5,397,709, U.S. Pat. No. 5,344,417, U.S. Pat. No. 5,374,264, U.S. Pat. No. 6,709,857; and U.S. Pat. No. 7,211,430.

In detection instruments such as the BacT/ALERT 3D and similar instruments, once the blood culture bottle has been tested positive for microorganism presence, it is difficult to obtain a high level of characterization of the microbial agent, or identification of the species of the microbial agent, due to the interference of blood components and artifacts of the disposable system (e.g., bottle) containing the sample. Therefore, current methods use a bottle or other suitable disposable container and a related instrument for natural growth and detection of a microorganism in the sample, as described above. Once the instrument indicates that the bottle is positive for presence of a microbial agent, according to current methods the "positive" bottle is manually retrieved from the instrument and a portion of the sample is manually removed from the bottle and cultured on an agar plate. There are instruments in the art that automate the streaking of a sample medium on a culture plate and incubating the plate. One such instrument is described in U.S. Pat. No. 6,617,146. After streaking, the plate is manually placed in an incubator and periodically inspected for growth of a subculture of the microorganism. After the subculture has grown sufficiently, a sample of the culture is taken from the plate and placed in a test tube. The test tube is then introduced into yet another instrument for identification testing via a disposable test sample card having a multitude of individual wells. The disposable test cards are known in the patent literature, see e.g., U.S. Pat. Nos. 4,118, 280, 3,963,355, 4,018,65; 4,116,775 and 4,038,151, 5,609, 828, 5,746,980, 5,766,553, 5,843,380, 5,869,005, 5,916,812, 5,932,177, 5,951,952, and 6,045,758, the entire content of which is incorporated by reference herein.

The test sample card is then processed in an analytical instrument known in the art as the VITEK 2 instrument of the assignee. The VITEK 2 instrument incubates and periodically reads the wells of the test sample card with a reader unit. Growth of the sample in one or more of the wells of the cards results in identification of the microbial agent. The VITEK 2 instrument is described in the patent literature, see e.g., U.S. Pat. Nos. 5,762,873 and 6,086,824, the content of which is incorporated by reference herein.

This entire process from the time of introducing the sample into the blood collection bottle to culture, detection of microorganism presence, and then identification of the microorganism by the VITEK 2 instrument typically takes 2-5 days. The identification steps alone, occurring after positive bottle detection, typically occupy 1-3 of these days.

Substantial, and potentially life saving, clinical benefits for a patient are possible if the time it takes for detection and identification of a microbial agent in a blood sample and reporting the results to a clinician could be reduced from the current 2-5 days to less than one day. This document discloses a method for rapid identification and/or characterization of a microbial agent in a biological sample such as a blood sample using a taxonomical hierarchical classification method.

SUMMARY

In a first aspect, a method is disclosed for identification and/or characterization of a microbial agent present in a sample. The method includes the steps of obtaining intrinsic fluorescence values over a range of emission wavelengths from the microbial agent. The fluorescence values are obtained at a plurality of excitation wavelengths. The intrinsic fluorescence measurements are subject to a transformation operation, thereby minimizing strain to strain variations in intrinsic fluorescence measurements within an organism group. Examples of the transformation operations include a natural logarithm transformation and a first derivative operation. With the aid of a programmed computer, the method includes a step of performing a multi-level classification algorithm coded as a set of processing instructions operating on the transformed intrinsic fluorescence measurements. The multiple levels corresponding to different levels in a taxonomic hierarchy for microbial agents suspected of being in the sample.

In one embodiment, the multi-level classification algorithm proceeds monotonically in an order from a higher level in the taxonomic hierarchy to a lower level in the taxonomic hierarchy. For example, the multi-level classification algorithm first classifies the microbial agent by Gram class, then family, and then species.

In one embodiment, the multi-level classification algorithm includes, for each level in the algorithm, steps of: (a) performing a distance calculation on transformed fluorescence values and an inverse of a covariance matrix for a pre-defined set of excitation/emission pairs; (b) performing a classification interpretation using the results of the distance calculation and a minimum distance threshold and a low discrimination threshold; and (c) generating a classification result. The pre-defined set of excitation/emission pairs are obtained from intrinsic fluorescence measurements from known microbial agents across a range of excitation and emission values, with the pre-defined set of excitation/emission pairs selected for their ability to distinguish between different microbial agents.

In another aspect, a method is disclosed for identification and/or characterization of a microbial agent present in a sample, comprising the steps of: experimentally obtaining intrinsic fluorescence measurements from known microbial agents across a range of excitation and emission values and selecting from such measurements a set of excitation/emission pairs for their ability to distinguish between different microbial agents; obtaining intrinsic fluorescence measurements from an unknown microbial agent at the set of excitation/emission pairs; transforming the intrinsic fluorescence measurements from an unknown microbial agent thereby minimizing strain to strain variations in intrinsic fluorescence measurements within an organism group; and identifying and/or characterizing the unknown microbial agent using the transformed intrinsic fluorescence measurements and the experimentally obtained intrinsic fluorescence measurements from known microbial agents with the aid of a programmed computer executing a classification algorithm.

In a preferred embodiment, the classification algorithm comprises a multi-level classification algorithm coded as a set of processing instructions operating on the transformed intrinsic fluorescence measurements, the multiple levels corresponding to different levels in a taxonomic hierarchy for microbial agents suspected of being in the sample.

The methods are applicable to microbial agents and samples generally. In one possible implementation, the samples are samples of human or animal blood and the microbial agents are agents (e.g., bacteria) present in the blood.

The taxonomic hierarchical classification method can be used with different analytical data besides microbial fluorescence data. Generalizing the disclosure, a method for rapid identification and/or characterization of a microbial agent present in a sample is disclosed, comprising the steps of: obtaining analytic test data of the microbial agent (e.g., mass spectrometry or Raman scattering data); transforming the analytic test data, thereby minimizing strain to strain variations in analytic test data within an organism group; and with the aid of a programmed computer, performing a multi-level classification algorithm coded as a set of processing instructions operating on the transformed analytic test data, the multiple levels corresponding to different levels in a taxonomic hierarchy for microbial agents suspected of being in the sample.

In still another aspect, a method for identification and/or characterization of a microbial agent present in a sample is disclosed, comprising the steps of: experimentally obtaining analytical test data from known microbial agents and selecting from such test data a subset of the test data for its ability to distinguish between different microbial agents; obtaining analytical test data from an unknown microbial agent associated with the subset of analytical test data; transforming the analytical test data from the unknown microbial agent thereby minimizing strain to strain variations in intrinsic fluorescence measurements within an organism group; and identifying and/or characterizing the unknown microbial agent using the transformed analytical test data and the experimentally obtained analytical test data from known microbial agents with the aid of a programmed computer executing a classification algorithm.

BRIEF DESCRIPTION OF THE DRAWINGS

FIGS. 2A-2C are a flow chart showing a sequence of processing instructions which perform identification and/or characterization of the concentrated microbial agent using intrinsic fluorescence measurements.

FIGS. 9 and 10 are plots of the first derivative of natural logarithm transforms of IF measurements showing the discrimination potential between a subset of species for excitation wavelengths of 315 and 415 nm.

DETAILED DESCRIPTION

Methods are described herein for identification and or characterization of a microbial agent. In preferred embodiments, the identification and/or characterization is performed on a concentrated microbial agent which has been isolated from other components in a sample. The method can be performed within while the concentrated microbial agent is stored in a disposable device used for separation and concentration of the microbial agent; alternatively it can be performed after the microbial agent has been removed from the disposable device. Examples of methods, instruments, and devices for separation and concentration of a microbial agent in a sample, e.g., blood, are described in the co-pending application Ser. No. 12/800,388, entitled "System for rapid identification and/or characterization of a microbial agent in a sample", which is incorporated by reference herein. Such methods, instruments and devices are not particularly important to the methods of this disclosure and therefore a detailed description is not provided so as to not obfuscate the present disclosure.

Figure 1:
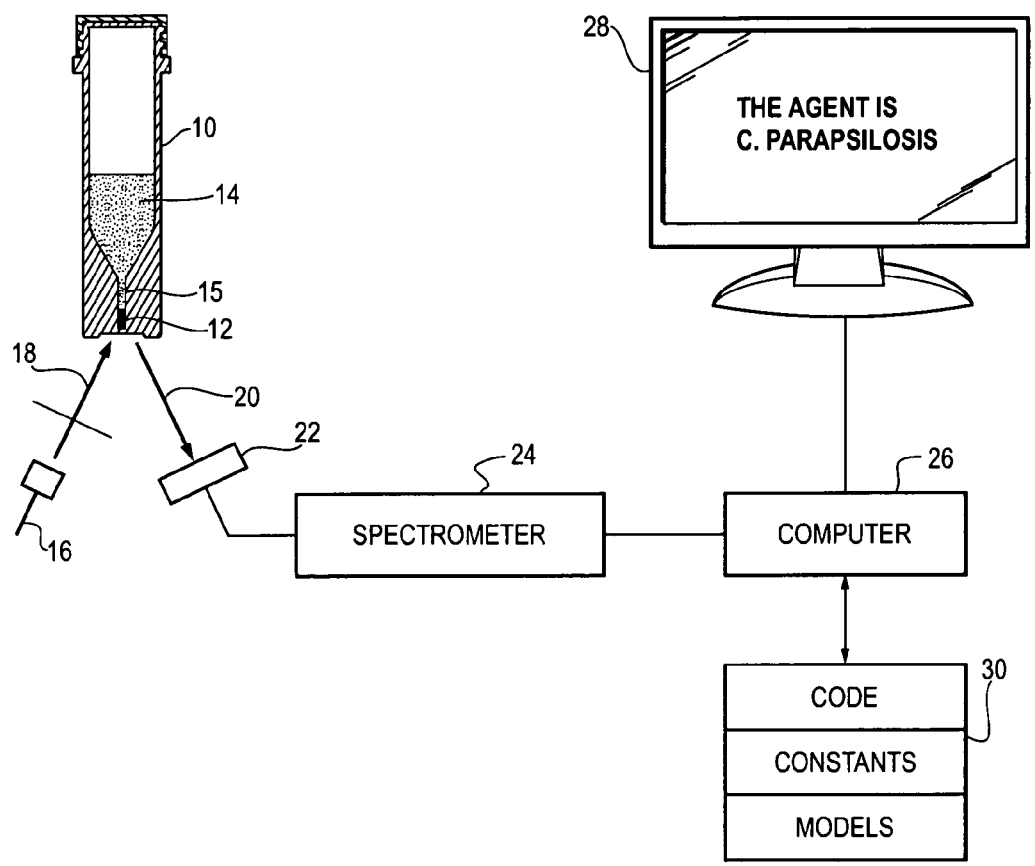
FIG. 1 is a schematic illustration of a measurement apparatus in which the methods of this disclosure may be used.

One representative example of a detection arrangement and disposable device will be described now in conjunction with FIG. 1. FIG. 1 is a schematic illustration of a measurement apparatus in which the methods of this disclosure may be used. The apparatus includes a disposable separation and concentration device 10 into which a sample 14 containing an unknown microbial agent is placed. The microbial agent is concentrated into an pellet-like mass 12 using optional selective lysis of non-microbial agent components in the sample, (e.g., blood cells) a density cushion present in the device 10 and centrifugation. The density gradient and centrifugation concentrate the microbial agent in the bottom of a capillary tube 15 present in the device 10.

The measurement apparatus includes a light source 16 emitting light 18 at an excitation wavelength to stimulate production of intrinsic fluorescence from the microbial agent 12. Emission radiation 20 is directed onto a sensor array 22 which is optionally coupled to a spectrometer 24. Fluorescence emission data in a band of wavelengths are sent to a computer 26. The computer is coupled to a memory 30 storing program code (including code executing the sequence of processing instructions shown in FIGS. 2A-2C), constants used in the modules, and models comprising a list of expected microbial agents and experimentally obtained fluorescence data in particular excitation and emission pairs which are discriminatory between microorganisms in the manner described below. The computer 26 processes the data with the aid of the information and code stored in memory 30 and generates a classification result which is displayed on an attached workstation display 28 or other suitable output device, the details of which are not important.

The separation, concentration and interrogation methods are described in further detail in the following applications, the contents of which are incorporated by reference herein, U.S. Ser. No. 12/589,929, entitled "Methods for the isolation and identification of microorganisms", filed Oct. 30, 2009; U.S. Ser. No. 12/589,969, entitled "Separation device for use in the separation, identification and/or characterization of microorganisms", filed Oct. 30, 2009; U.S. Ser. No. 12/589,952, entitled "Method for separation, identification and/or characterization of microorganisms using spectroscopy", filed Oct. 30, 2009; U.S. Ser. No. 12/589,936, entitled "Method for separation, identification and/or characterization of microorganisms using mass spectrometry", filed Oct. 30, 2009; U.S. Ser. No. 12/589,985, entitled "Method for separation and characterization of microorganisms using identifier agents", filed Oct. 30, 2009; U.S. Ser. No. 12/589,968, entitled "Method for detection, identification and/or characterization of microorganisms in a sealed container", filed Oct. 30, 2009; U.S. Ser. No. 12/589,976, entitled "Method for separation, identification and/or characterization of microorganisms using Raman spectroscopy", filed Oct. 30, 2009. the present inventive methods are not limited to these techniques.

Once the microorganism or other microbial agent present in the sample has been isolated and/or pelleted in the separation device 10, the isolated sample or pellet is interrogated (e.g., spectroscopically, using intrinsic fluorescence measurements) as described below to characterize and/or identify the microorganisms in the sample or pellet. The interrogation can take place in a non-invasive manner, that is, the pellet can be interrogated while it remains in the device 10 used to separate and concentrate the microbial agent. The ability to identify the microorganisms in a non-invasive manner, optionally coupled with keeping the device 10 sealed throughout the separation and characterization/identification process and automating the procedure avoids the constant handling of contaminated and/or infectious samples and greatly increases the safety of the entire process. Furthermore, the ability to characterize and/or identify microorganisms by direct interrogation without further processing of the sample or pellet 12 (e.g., re-suspension, plating, and growth of colonies), greatly increases the speed with which identification/characterization can be made.

In one embodiment, optical spectroscopic methods can be used to analyze one or more intrinsic properties of the microorganisms, e.g., a property present within the microorganism, in the absence of additional agents, such as stains, dyes, binding agents, etc. In other embodiments, the optical spectroscopic methods can be used to analyze one or more extrinsic properties of the microorganisms, e.g., a property that can only be detected with the aid of additional identifier agents. The interrogation in preferred forms is carried out using fluorescence spectroscopy. For example, front face fluorescence (where the exciting and emitted light enters and leaves the same optical surface, and if the sample is generally optically thick, the excitation light penetrates a very short distance into the sample (see, e.g., Eisinger, J., and J. Flores, "Front-face fluorometry of liquid samples," Anal. Biochem. 94:15 (1983)) can be used for identification of microorganisms in pellets.

Typically, the light source 16, or excitation source, results in the excitation of the sample, followed by measurement of the emission of fluorescence 20 of the sample at predetermined time points or continuously. Similarly, the reflected light from interaction of the excitation source with the sample may be measured to provide pertinent data for identification and/or characterization. The emission from the sample may be measured by any suitable means of spectral discrimination, most preferably employing a spectrometer 24.

In a presently preferred embodiment, control measurements (e.g., fluorescence spectra) are taken for known microorganisms and data stored in the memory 30, thus allowing for correlation of measured test data with characterization of the microorganisms of interest using various mathematical methods known to those skilled in the art. The measured test data from known microorganisms is stored in machine-readable memory 30, e.g., within an instrument implementing the method or within an associated data processing device, such as connected workstation. These methods may be used to classify unknown microorganisms of interest in the sample being tested into relevant groups (e.g., species) based on existing nomenclature, and/or into naturally occurring groups based on the organism's metabolism, pathogenicity and/or virulence in designing the system for monitoring, detecting and/or characterizing the organism as described previously.

The sample illumination source (See FIG. 1), or excitation source 16, may be selected from any number of suitable light sources as known to those skilled in the art. Any portion of the electromagnetic spectrum that produces usable data can be used. Light sources capable of emission in the ultraviolet, visible and/or near-infrared spectra, as well as other portions of the electromagnetic spectrum, can be utilized and are known to those skilled in the art. For example, light sources may be continuum lamps such as a deuterium or xenon arc lamp for generation of ultraviolet light and/or a tungsten halogen lamp for generation of visible/near-infrared excitation. These light sources provide a broad emission range and the spectral bandwidth for specific excitation wavelengths may be reduced using optical interference filters, prisms and/or optical gratings, as are well known in the art.

Alternatively, a plurality of narrowband light sources, such as light emitting diodes and/or lasers, may be spatially and/or temporally multiplexed to provide a multi-wavelength excitation source. For example, light emitting diodes are available from 240 nm to in excess of 900 nm and the sources have a spectral bandwidth of 20-40 nm (full width at half maximum). Lasers are available in discrete wavelengths from the ultraviolet to the near-infrared and can be employed using multiplexing methods well known to those skilled in the art.

The spectral selectivity of any of the light sources may be improved by using spectral discrimination means such as a scanning monochromator. Other methods of discrimination may be utilized, as known to those of skill in the art, such as an acousto-optic tunable filter, liquid crystal tunable filter, an array of optical interference filters, prism spectrograph, etc., and in any combination. A consideration in selecting the spectral discriminator takes into the account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Illumination from the light source 16 results in the excitation of the sample, followed by measurement of the emission of fluorescence of the sample at predetermined time points or continuously. Similarly, the reflected light from interaction of the excitation source with the sample may be measured to provide pertinent data for detection and/or characterization.

The emission from the sample may be measured by any suitable means of spectral discrimination, most preferably employing a spectrometer 24. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device (CCD) detector array. In one embodiment, a discriminator allows the observation of the fluorescence and/or scattering signal by a photodetection means (such as a photomultiplier tube, avalanche photodiode, CCD detector array, and/or electron multiplying charge coupled device (EMCCD) detector array).

The spectroscopic technique is used to obtain measurements that are preferably provided as Excitation-Emission Matrix (EEM) measurements. As used herein, EEM is defined as the luminescent spectral emission intensity of fluorescent substances as a function of both excitation and emission wavelength, and includes a full spectrum or a subset thereof, where a subset may contain a single or multiple excitation/emission pairs(s). Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at more than one specific excitation-emission wavelength pair, e.g., at least at 2, 3, 4, 5, 6, 7, 8, 9, 10, or more specific excitation-emission wavelength pairs.

It has been found that a front-face fluorescence spectroscopy provides an advantage in measuring the fluorescence and/or reflectance properties of highly scattering and highly quenching samples. In one embodiment, the front-face method may be particularly useful. For example, front-face fluorescence may be particularly useful in highly absorbent samples because the excitation and emission beam does not need to travel through the bulk of the sample, and thus, may be less affected by the interfering components that may be contained therein (e.g., blood cells and microbiological culture media). The optical surface of the separation device 1904 may be illuminated at such an angle as to provide acceptable results as known to those skilled in the art, (e.g., Eisinger, J., and J. Flores, "Front-face fluorometry of liquid samples," Anal. Biochem. 94:15-21 (1983)). In one embodiment, the system is designed such that the spectroscopic system measures diffuse reflected light at a minimum of one fixed angle in addition to measuring emitted fluorescence at a minimum of one fixed angle.

In some embodiments, characterization and/or identification of the microorganisms in the isolated sample or pellet need not involve identification of an exact species. Characterization encompasses the broad categorization or classification of biological particles as well as the actual identification of a single species. Classification of microorganism from an isolated sample or pellet may comprise determination of phenotypic and/or morphologic characteristics for the microorganism. For example, characterization of the biological particles may be accomplished based on observable differences, such as, composition, shape, size, clustering and/or metabolism. In some embodiments, classification of the biological particles of interest may require no prior knowledge of the characteristics of a given biological particle but only requires consistent correlations with empiric measurements thus making this method more general and readily adaptable than methods based on specific binding events or metabolic reactions. As used herein "identification" means determining to which family, genus, species, and/or strain a previously unknown microorganism belongs to. For example, identifying a previously unknown microorganism to the family, genus, species, and/or strain level.

In some instances, characterization encompasses classification models which provide sufficient useful information for action to be taken. As used herein, the preferred classification models comprise grouping into one or more of the following: (1) Gram Groups; (2) Clinical Gram Groups; (3) Therapeutic Groups; (4) Functional Groups; and (5) Natural Intrinsic Fluorescence Groups.

(1) Gram Groups: Within the Gram Groups classification, microorganisms may be placed into one of three broad classification categories based on their Gram staining reaction and overall size, said groups selected from one or more of the following: (a) Gram positive microorganisms that stain dark blue with Gram staining; (b) Gram negative microorganisms that stain red with Gram staining; and (c) yeast cells that stain dark blue with Gram staining, but are very large rounded cells that are distinguished from bacteria by their morphological characteristics and size.

(2) Clinical Gram Groups: The Gram Groups may be further divided into several sub-categories representing distinguishing morphological features. These sub-categories comprise all the relevant clinical information reported by an experienced laboratory technologist, and thus provide a higher level of identification than a positive or negative Gram reaction. This particular classification is very helpful because it eliminates concerns about relying on the quality of a Gram stain and/or the skill level of the technician reading the smear by providing the equivalent clinically relevant information with an automated system. More specifically, subcategories of microorganisms based on this classification model may be selected from one or more of the following: (a) cocci, which are small rounded cells; (b) diplococci, which are two small rounded cells joined together; (c) rods, which are rectangular shape; and (d) bacilli, which are rod shaped. Examples of these sub-categories that can be ascertained by additional morphological information include: (i) Gram positive cocci; (ii) Gram positive cocci in chains; (iii) Gram positive cocci in clusters (i.e., "grape-like" clusters); (iv) Gram positive diplococci; (v) Gram positive rods; (vi) Gram positive rods with endospores; (vii) Gram negative rods; (viii) Gram negative coccobacilli; (ix) Gram negative diplococci; (x) yeast; and (xi) filamentous fungi.

(3) Therapeutic Groups: The therapeutic groups comprise multiple microbial species that, when isolated from particular specimen types, are treated with the same class of antibiotics or mixture of antibiotics (e.g., as described in "Sanford Guide to Antimicrobial Therapy 2008"). In many cases, identity to the species level is not required by the clinician to enable a change from initial empiric therapy to a more targeted therapy because more than one species can be treated with the same choice of antibiotic(s). This classification level correctly places these "same-treatment" microorganisms into single therapeutic categories. Examples of this characterization level include the ability to distinguish highly resistant Enterobacteriacae (EB) species from sensitive EB species (*Enterobacter* spp. from *E. coli*), or fluconazole-resistant *Candida* species (*C. glabrata* and *C. kruzei*) from sensitive *Candida* species (*C. albicans* and *C. parapsilosis*), and so on.

(4) Functional Groups: According to the invention, microorganisms may also be placed into several groups based upon a mixture of metabolic, virulence and/or phenotypic characteristics. Non-fermentative organisms may be clearly distinguished from fermentative ones. Furthermore, microorganism species that produce hemolysins may be grouped separately from non-hemolytic species. In some cases, these groups represent broader categories than genus level (e.g., coliforms, Gram negative non-fermentative rods), some at the genus level (e.g., *Enterococcus, Candida*), and some with closer to species-level discrimination (e.g., coagulase-negative staphylococci, alpha-hemolytic streptococci, beta-hemolytic streptococci, coagulase-positive staphylococci, i.e., *S. aureus*).

(5) Natural Intrinsic Fluorescence ("IF") Groups: Microorganisms may also be placed into categories based on their natural tendency to group together by their innate and/or intrinsic fluorescence characteristics. Some of these groups may be common to Therapeutic and Functional Group categories. These groupings may comprise individual species, such as *E. faecalis, S. pyogenes*, or *P. aeruginosa* that have characteristic IF signatures and/or may contain small groups of organisms with relatively conserved IF signatures such as the *K. pneumoniae-K. oxytoca* or *E. aerogenes-E. cloacae* groups.

In addition to measuring intrinsic properties of microorganisms (such as intrinsic fluorescence) for identification purposes, the methods may use additional identifier agents to aid in the separation and/or identification process. Agents that bind to specific microorganisms, such as affinity ligands, can be used to separate microorganisms, to identify a class or species of microorganism (e.g., through binding to a unique surface protein or receptor) and/or to identify a characteristic of the microorganism (e.g., antibiotic resistance). Useful identifier agents include, without limitation, monoclonal and polyclonal antibodies and fragments thereof (e.g., anti-Eap for *S. aureus* identification), nucleic acid probes, antibiotics (e.g., penicillin, vancomycin, polymyxin B), aptamers, peptide mimetics, phage-derived binding proteins, lectins, host innate immunity biomarkers (acute phase proteins, LPS-binding protein, CD14, mannose binding lectin, Toll-like receptors), host defense peptides (e.g., defensins, cathelicidins, proteogrins, magainins), bacterocins (e.g., lantibiotics, such as nisin, mersacidin, epidermin, gallidermin, and plantaricin C, and class II peptides), bacteriophages, and dyes selective for nucleic acids, lipids, carbohydrates, polysaccharides, capsules/slime or proteins, or any combination thereof. If the agent does not itself give out a detectable signal, the agent can be labeled to provide a detectable signal, such as by conjugating the agent to a marker (e.g., visible or fluorescent). Markers include, without limitation, fluorescent, luminescent, phosphorescent, radioactive, and/or colorimetric compounds. The agent can be added to the microorganisms at any step in the methods of the invention, e.g., when the sample is obtained, during lysis, and/or during separation. In some embodiments, the presence of the agent in the pellet can be determined during interrogation of the pellet. Other useful identifier agents include substrates for microbial enzymes, chelating agents, photosensitizing agent, quenching agent, reducing agent, oxidizing agent, buffer, acid, base, solvent, fixative, detergents, surfactants, disinfectants (eg. alcohols, bleach, hydrogen peroxide) and toxic compounds (eg. sodium azide, potassium cyanide) and metabolic inhibitors such as cyclohexamide, etc. Similarly, many fluorescent compounds for measuring microbial cell viability, metabolism and/or membrane potential may be used as an identifier agent in the present invention. As would be readily appreciated by one of skill in the art, the sensitivity of a particular microorganism to any compound affecting its physical state or metabolism, such as an antibiotic, could be rapidly ascertained by adding the compound to the sample, lysis buffer, density cushion or any mixture thereof.

An embodiment of a method for performing identification and/or characterization of microbial agents in samples using intrinsic fluorescence and a hierarchical taxonomic classification process will now be described in conjunction with FIGS. 2-10. Basically, the method can be embodied as a sequence of processing instructions stored in memory and executed using a conventional data processor or computer 26. The processing instructions execute an algorithm shown in FIGS. 2A-2C which is designed to provide the identification of a blood culture isolate (concentrated pellet) given an intrinsic fluorescence (IF) scan of the isolate from a predefined set of emission wavelengths. The algorithm can be adapted for other types of analytical test data (e.g., Raman scattering or mass spectrometry).

In preferred embodiments, the method is encoded as software instructions implementing a multi-level identification algorithm. Traditional classification algorithms that take input data and determine the identification of a microorganism use a single classification model. Given data from an intrinsic fluorescence scan at a predefined set of wavelengths of an unknown organism, the multi-leveled identification algorithm classifies the organism following the branches of a taxonomic hierarchy—Gram class, family, and species. A unique feature is the use of separate classification models at each identification step from highest, Gram class, to lowest, species level Additionally, the approach incorporates the use of parallel classification models to evaluate consistency between results. Thus, the probability of accurate identification and/or characterization is maximized, and generation of incorrect identification or characterization results is minimized.

Figure 2A:
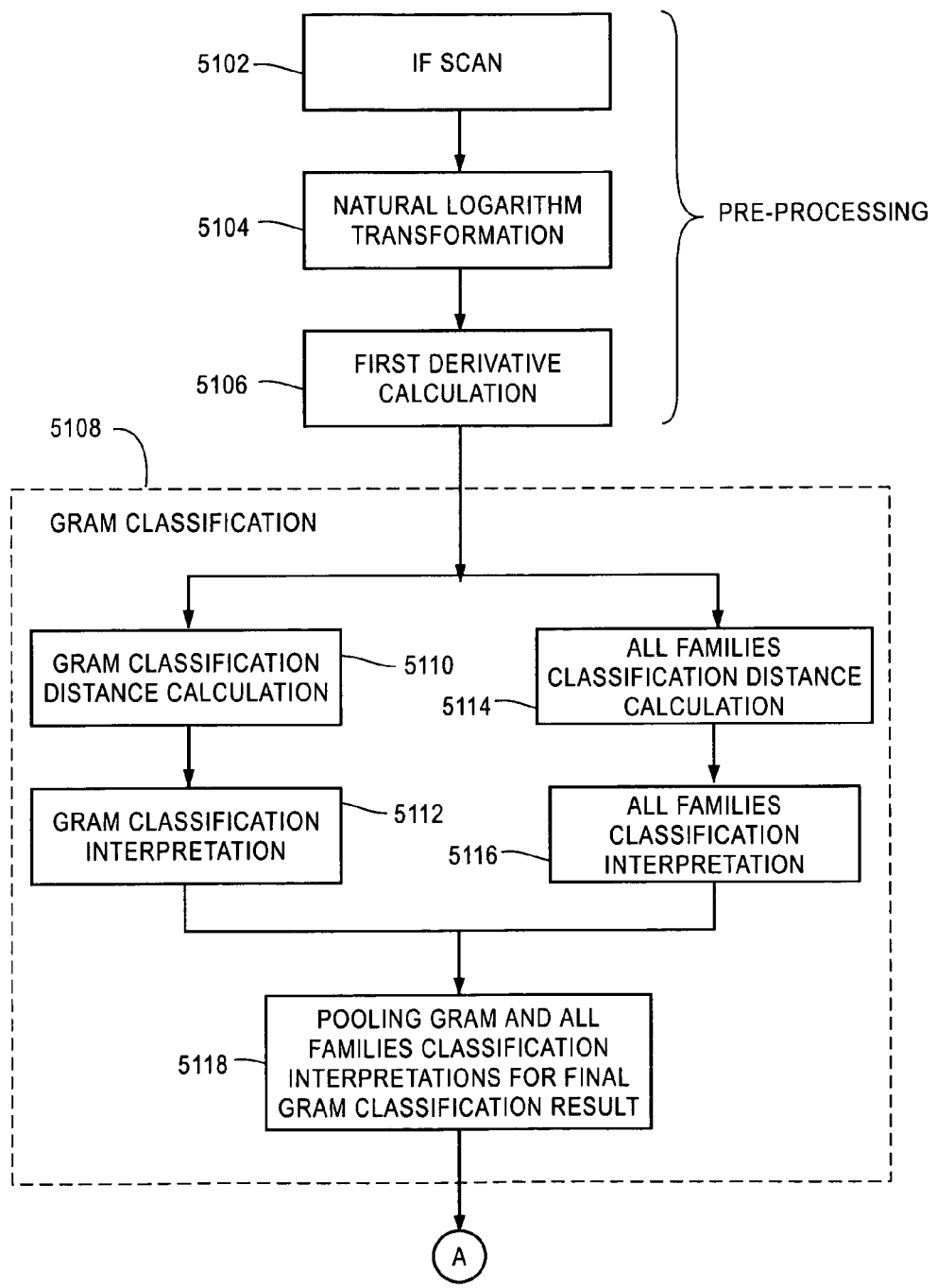
Figure 2B:
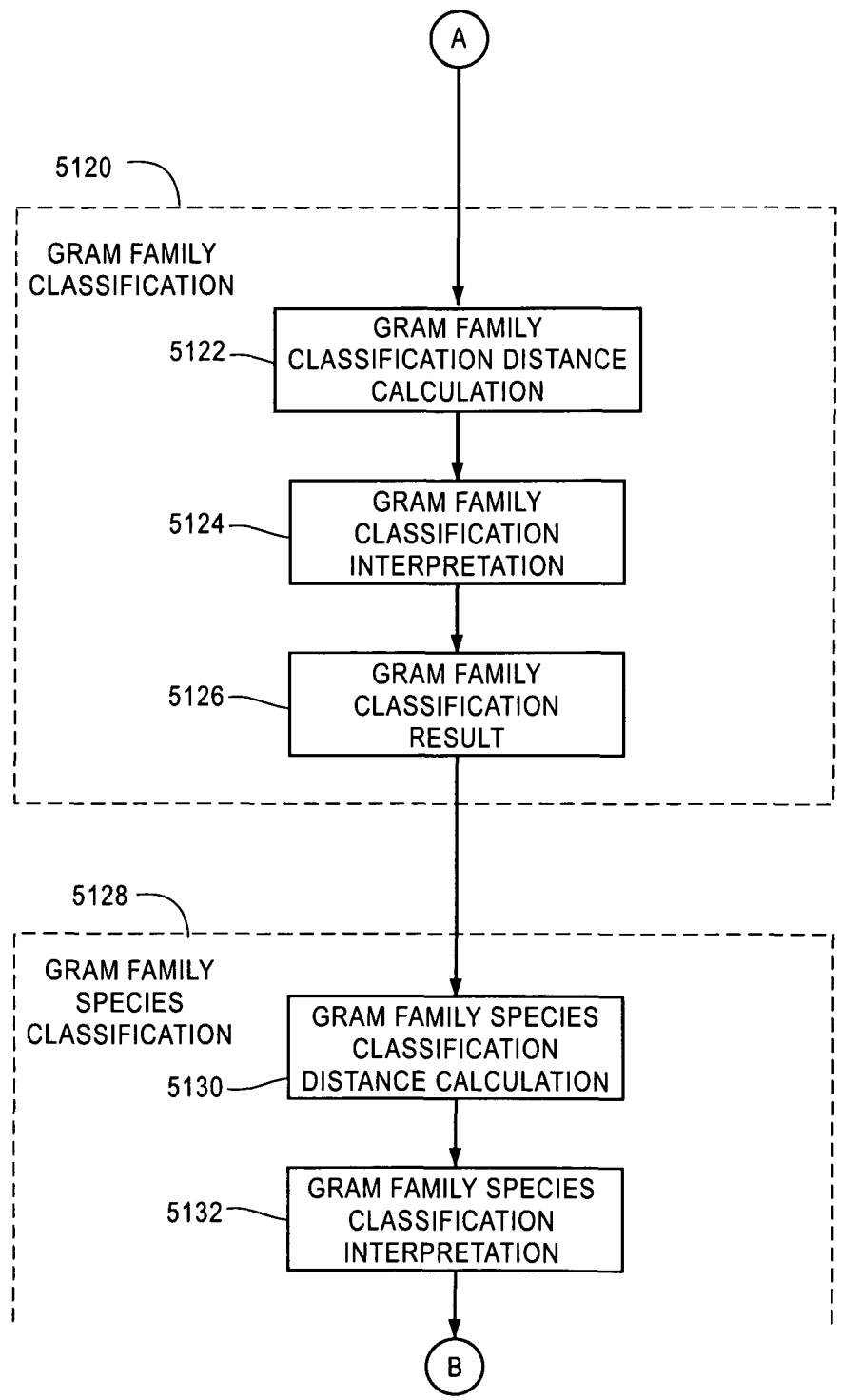

The identification method includes a set of data pre-processing steps (shown as blocks 5102, 5104 and 5106 of FIG. 2A, and a set of analysis steps (the remaining blocks 5108, 5110, etc. in FIGS. 2B, 2C). The method determines the identification of the organism at multiple levels of the taxonomic hierarchy. The pre-processing steps are designed to acquire IF scan data and perform data transformations that minimize variation between different strains of a microbial agent within a given organism group or species. The data analysis steps implement a multi-level identification using parallel classification models, as will be understood from the following discussion.

As noted above, preferred embodiments provide an organism identification at the Gram, family, and species levels. Organisms commonly found in blood cultures that can be identified by the algorithm include, but not necessarily limited to, those listed in Table 1. Obviously, for different applications (e.g., food, water, environmental samples, etc.) the organisms may differ from those listed in Table 1, however the methodology is the same.

TABLE 1

Intrinsic Fluorescence Algorithm Identification Organism List

| Gram Class | Family | Species |
|---|---|---|
| Gram-negative | Enterobacteriaceae | C. freundii |
| | | E. aerogenes |
| | | E. cloacae Complex |
| | | E. coli |
| | | K. oxytoca |
| | | K. pneumoniae |
| | | M. morganii |
| | | P. mirabilis |
| | | P. stuartii |
| | | P. vulgaris |
| | | S. enteritidis |
| | | S. marcescens |
| | Moraxellaceae | A. baumanii |
| | Neisseriaceae | N. meningitidis |
| | Pasteurellaceae | H. influenzae |
| | Pseudonomadaceae | P. aeruginosa |
| | Xanthomonadaceae | S. maltophilia |
| Gram-positive | Enterococcaceae | E. faecalis |
| | | E. faecium |
| | Listeriaceae | L. monocytogenes |
| | Staphylococcaceae | S. aureus |
| | | S. capitis |
| | | S. epidermidis |
| | | S. hominis |
| | | S. lugdunensis |
| | | S. warneri |
| | Streptococcaceae | S. agalactiae |
| | | S. bovis |
| | | S. mitis/S. oralis |
| | | S. pneumoniae |
| | | S. pyogenes |
| Yeast | Ascomycetes | C. albicans |
| | | C. glabrata |
| | | C. krusei |
| | | C. parapsilosis |
| | | C. tropicalis |

The processing steps or modules shown in FIGS. 2A-C will now be described in detail.

Pre-Processing

Step 5102: Obtain a fluorescence value, $n_{ij}$, for each excitation value, i=1, 2, . . . , x, and each emission, j=1, 2, . . . , y, combination. The ratio, emission value/excitation value, must fall within the interval (1.05, 1.95).

Step 5104: For each fluorescence value, $n_{ij}$, calculate the natural logarithm value, ln ($n_{ij}$).

Step 5106: Calculate the $1^{st}$ derivative of the natural log transform value (from step 5104) for each emission value, j=2, 3, . . . , y−1, across a given excitation wavelength, i.

Figure 3:
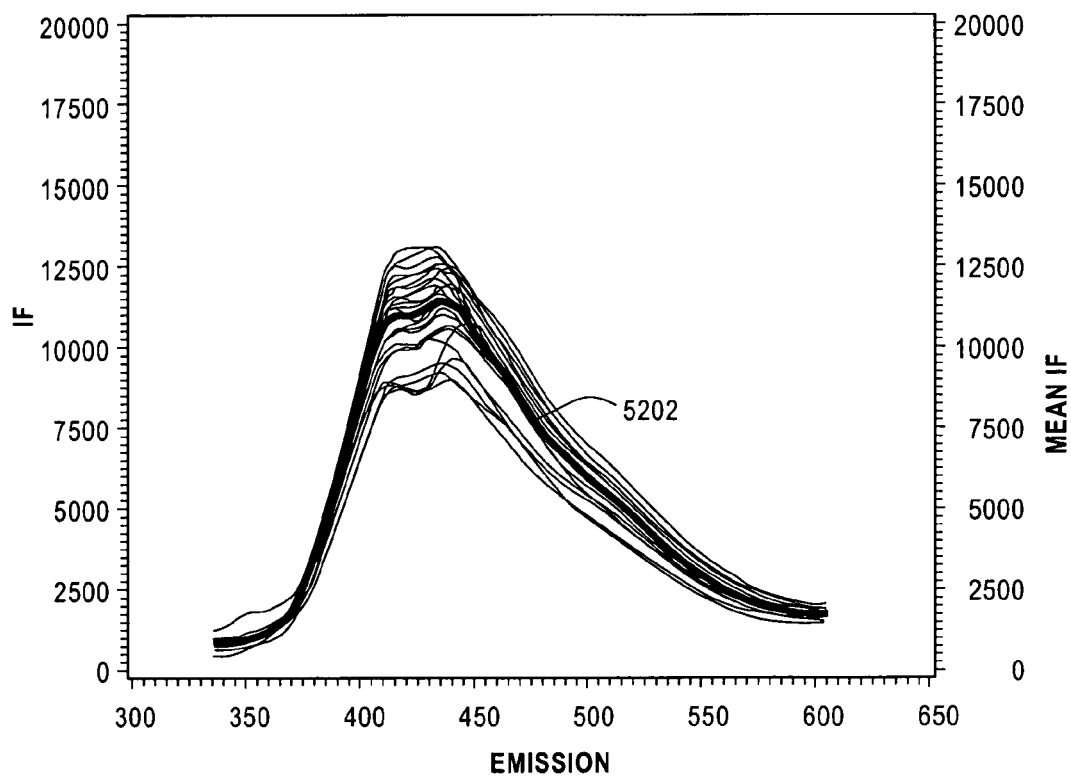
FIGS. 3-8 are plots of intrinsic fluorescence (IF) measurements, and transforms thereof which illustrate the benefit of the pre-processing instructions of FIG. 2A in terms of minimizing strain-to-strain variations within an organism group.
Figure 4:
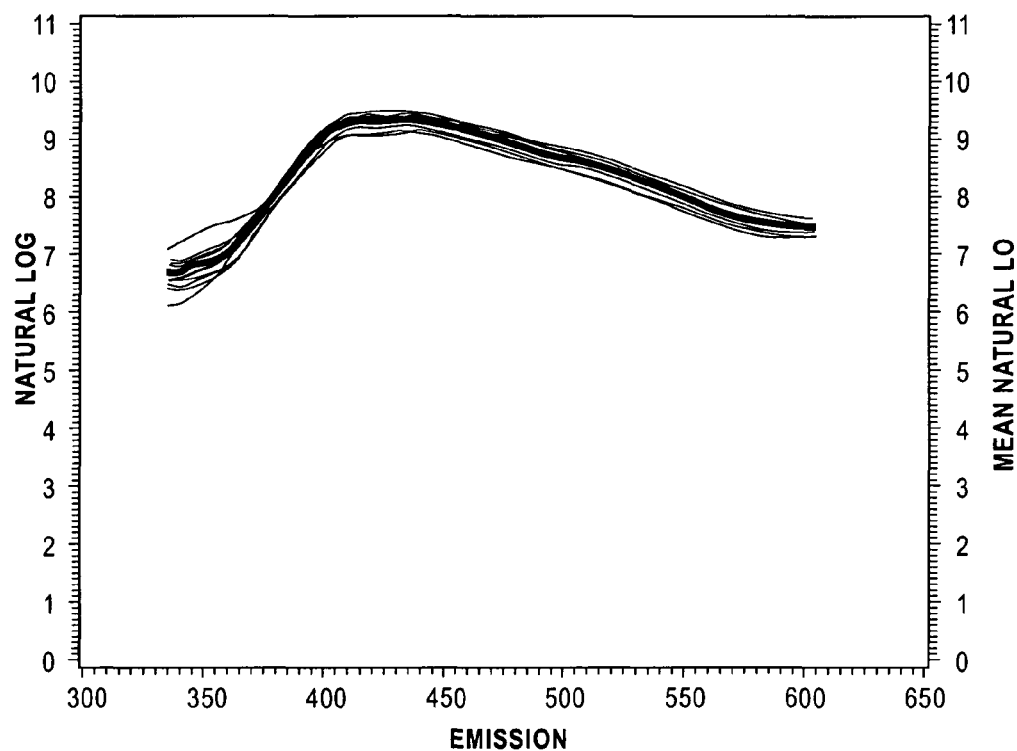
Figure 5:
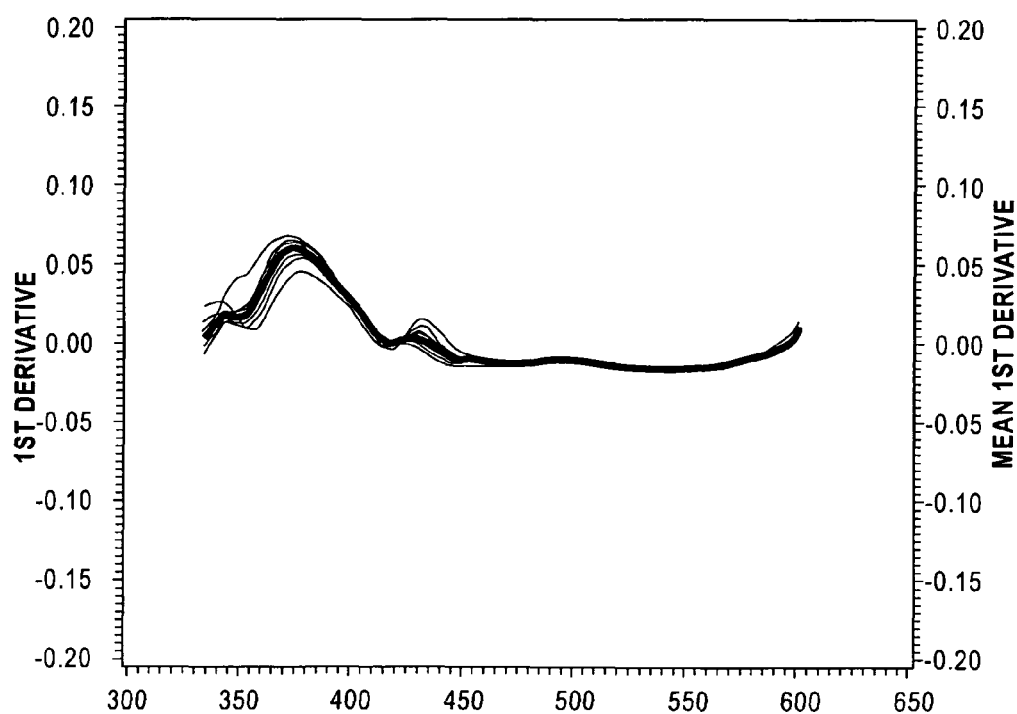

It is advantageous to transform the raw fluorescence data to minimize strain-to-strain variation within each organism group, using both steps 5104 and 5106. Additionally, the transformation process tends to create similar variance across organism groups. FIGS. 3, 4 and 5 illustrate by way of example the effects of performing the described pre-processing for multiple strains of *Staphylococcus aureus* evaluated across the emission range at excitation 315. In FIG. 3, each line represents the fluorescence signal from a single strain. The line 5202 indicates the mean fluorescence signal at each emission value. FIG. 4 shows the strain-to-strain variation in the fluorescence signal after application of the natural logarithm transformation (step 5104); note that the curve shape for all of the strains are close together. FIG. 5 shows the strain-to-strain variation at excitation of 315 nm after calculation of the first derivative of the natural logarithm transform (step 5106). Again, note that the curve shape for all the strains are very close together, particularly at the emission range of 400-610 nm.

Figure 6:
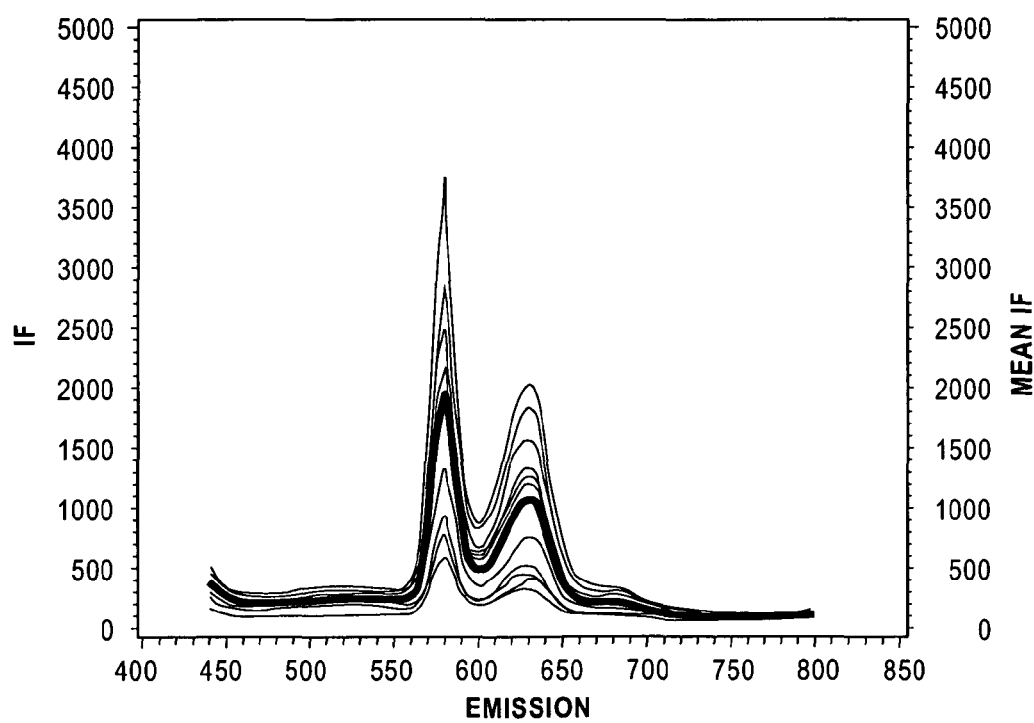
Figure 7:
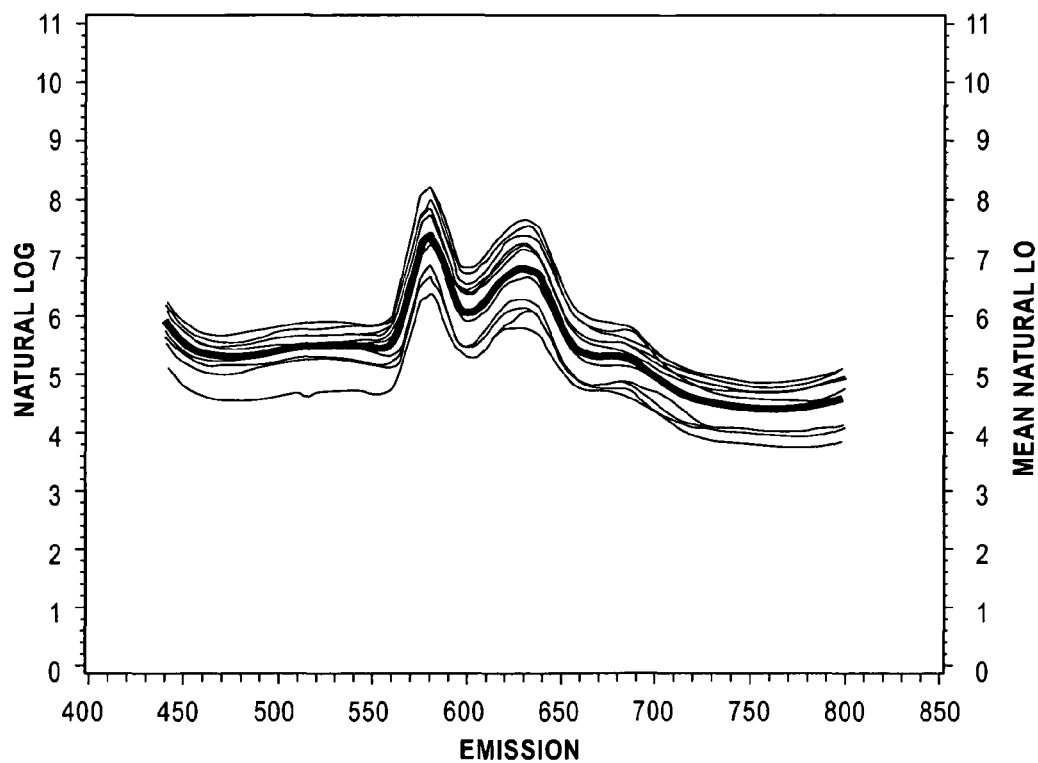
Figure 8:
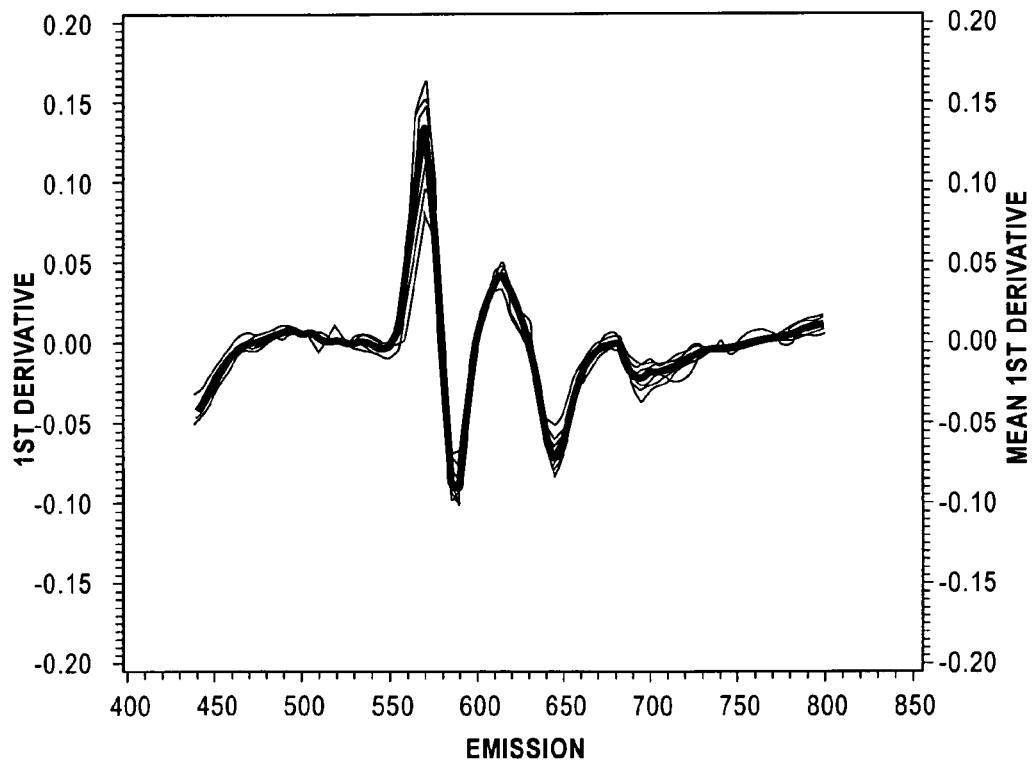

As another example, FIG. 6 shows the strain-to-strain variation in the fluorescence signal at excitation of 415 nm for *Candida parapsilosis*, prior to performing the transformation steps. Note the wide variation in emission in the range of 400-650 nm. Strain-to-strain variation for this organism at excitation of 415 nm after performing the natural logarithm transformation is shown in FIG. 7. Strain-to-strain variation after performing the first derivative transformation is shown in FIG. 8. Note that in FIG. 8 the strain-to-strain variation is much reduced.

Additional data transformations may be used. One is to normalize the fluorescence value at each emission point to the average for all emission pairs for a particular excitation wavelength.

In another pre-processing approach, a normalizing of the fluorescence value to the maximum signal along each emission and/or excitation wavelength line may identify nearby non-peak regions of the spectrum that provide considerable classification benefit not possible with non-normalized data. In some cases, it may be more accurate to first normalize the fluorescence value to a less variable cellular fluorophore, such as tryptophan before applying other normalization and/or analysis strategies. Furthermore, Rayleigh scattering (diffuse reflectance) data may potentially be used to compensate for surface variations in the separation device and/or variations within the microbial cell pellet and/or optical system.

Analysis

Step 5108: The first level of classification in the analysis after performing the pre-processing steps is gram classification 5108. At this step, the processing includes two branches, one represented by steps 5110 and 5112 and another represented by steps 5114 and 5116. FIG. 2A is not meant to imply that the branches could not be performed sequentially; the branches could be performed either sequentially or in parallel.

Step 5110: Gram Classification Distance Calculation. Using the $1^{st}$ derivative transforms for a predefined set of excitation/emission pairs, calculate the distance, $$d_a = [(m-m_a)^t \Sigma^{-1} (m-m_a)]^{1/2}$$

for each Gram class defined in the model
where
a=1, 2, 3, represents the Gram classes defined in the model
m represent the vector of calculated values of the $1^{st}$ derivative, $m_{ij}$, of the natural log transform for each excitation/emission pair i, j
$m_a$ represent the vector of mean values $m_{a(ij)}$ from a distribution for each class a at excitation/emission pair i, j
t represent the transpose of the vector
(m−$m_a$) represent the vector of differences $m_{ij}-m_{a(ij)}$ for each excitation/emission pair i, j
$\Sigma^{-1}$ represents the inverse of the covariance matrix for the predefined set of excitation/emission pair. The set of excitation and emission pairs are experimentally determined from fluorescence measurements (with preprocessing performed) of known microorganisms (see FIGS. 9 and 10 and the discussion below).

The term "model" is used to refer to a set of known microbial agents for which IF measurements (including transforms) at the predetermined excitation wavelengths have been previously obtained and for which a specimen is a candidate for classification, e.g., the agents listed in Table 1.

Step 5112: Gram Classification Interpretation.

Let $u_g$ represent the maximum distance threshold

If all distances, $d_1$, $d_2$, and $d_3$, are greater than $u_g$, the classification result is Unknown Else, determine the value of $d_{min}$, the minimum value of $d_1$, $d_2$, and $d_3$ Let $w_g$ represent the low discrimination threshold factor If more than one distance, $d_1$, $d_2$, and $d_3$, is less than $(d_{min}*w_q)$, the classification result is Low Discrimination between the Gram classes having distances less than $(d_{min}*w_q)$ If only one distance, $d_1$, $d_2$, and $d_3$, is less than $(d_{min}*w_q)$, the classification result is the corresponding Gram class.

Step 5114: All Families Classification Distance Calculation

Using the 1$^{st}$ derivative transforms for a predefined set of excitation/emission pairs, calculate the distance, $$d_a = [(m-m_a)^t \Sigma^{-1} (m-m_a)]^{1/2}$$

for each organism family defined in the model where a=1, 2, . . . , k, represents all of the organism families defined in the model $\Sigma^{-1}$ represents the inverse of the covariance matrix for the predefined set of excitation/emission pairs (same remark as above, the set of excitation and emission pairs are experimentally determined)

m represent the vector of calculated values of the 1$^{st}$ derivative, $m_{ij}$, of the natural log transform for each excitation/emission pair i, j $m_a$ represent the vector of mean values $m_{a(ij)}$ from a distribution for each class a at excitation/emission pair i, j t represent the transpose of the vector $(m-m_a)$ represent the vector of differences $m_{ij}-m_{a(ij)}$ for each excitation/emission pair i, j Step 5116: All Families Classification Interpretation Let $u_f$ represent the maximum distance threshold If all distances, $d_1$, $d_2$, $d_a$, are greater than $u_f$, the classification result is Unknown Else, determine the value of $d_{min}$, the minimum value of $d_1$, $d_2$, $d_a$ Let $w_f$ represent the low discrimination threshold factor If more than one distance, $d_1$, $d_2$, . . . , $d_a$, is less than $(d_{min}, w_f)$; the classification result is Low Discrimination between the organism families having distances less than $(d_{min}*w_f)$ If only one distance, $d_1$, $d_2$, $d_a$, is less than $(d_{min}*w_q)$, the classification result is the corresponding family.

Step 5118: Pooling gram and all families classification interpretations for final gram classification result.

If the Gram classification is a single choice and the all families classification is a single choice, the pooled classification result is the indicated Gram class if the family classification falls under the taxonomic hierarchy of the Gram class.

If the Gram classification is a single choice and the all families classification is a single choice, the pooled classification result is Unknown if the family classification does not fall under the taxonomic hierarchy of the Gram class.

If the Gram classification is a single choice and the all families classification is a low discrimination, the pooled classification is the indicated Gram class if the family associated with the shortest distance falls under the taxonomic hierarchy of the Gram class.

If the Gram classification is a single choice and the all families classification is a low discrimination, the pooled classification is Unknown if the family associated with the shortest distance does not fall under the taxonomic hierarchy of the Gram class.

If the Gram classification is a low discrimination and the all families classification is a single choice, the pooled classification result is the Gram class that corresponds to the Gram class under which the family resides on the taxonomic hierarchy.

If the Gram classification is a low discrimination and the all families classification is a single choice, the pooled classification result is Unknown if none of the Gram classes correspond to the Gram class under which the family resides on the taxonomic hierarchy.

If the Gram classification and the all families classification are both Unknown, the pooled classification result is Unknown.

The processing then proceeds to step 5120, Gram Family Classification, a second, lower, level of classification in a taxonomic hierarchy. This step consists of sub-steps 5122, 5124 and 5126.

Step 5122: Gram family classification distance calculation.

Using the 1$^{st}$ derivative estimates for a predefined set of excitation/emission pair that are specific to the Gram classification result, calculate the distance, $$d_a = [(m-m_a)^t \Sigma^{-1} (m-m_a)]^{1/2}$$

for each organism family defined in the model, where a=1, 2, . . . , k, represents the number of organism families defined in the model $\Sigma^{-1}$ represents the inverse of the covariance matrix for the predefined set of excitation/emission pairs (same remark as before regarding the pairs)

m represents the vector of calculated values of the 1$^{st}$ derivative, $m_{ij}$, of the natural log transform for each excitation/emission pair i, j $m_a$ represent the vector of mean values $m_{a(ij)}$ from a distribution for each class a at excitation/emission pair i, j t represent the transpose of the vector $(m-m_a)$ represent the vector of differences $m_{ij}-m_{a(ij)}$ for each excitation/emission pair i, j Step 5124: Gram Family Classification Interpretation Let $u_t$ represent the maximum distance threshold If all distances, $d_1$, $d_2$, . . . , $d_a$, are greater than $u_t$, the classification result is Unknown Else, determine the value of $d_{min}$, the minimum value of $d_1$, $d_2$, . . . , $d_a$ Let $w_t$ represent the low discrimination threshold factor If more than one distance, $d_1$, $d_2$, . . . , $d_a$, is less than $(d_{min}*w_t)$, the classification result is Low Discrimination between the organism families having distances less than $(d_{min}*w_t)$ If only one distance, $d_1$, $d_2$, . . . , $d_a$, is less than $(d_{min}*w_t)$, the classification result is the corresponding family.

Step 5126 Gram Family Classification Result.

If the Gram family classification result is Unknown, the test organism classification is finalized at the Gram level.

If the Gram family classification result is Low Discrimination, the test organism classification is finalized as the Gram and families included in the low discrimination.

If the Gram family classification result a single family, the IF data from the test organism are further analyzed to determine if a species level identification can be determined.

Step 5128 Gram family Species Classification. The processing instructions proceed to a gram family species classification level, a third and even lower level of classification in a taxonomic hierarchy, consisting of sub-steps 5130, 5132, and 5134.

Step 5130 Gram family species classification distance calculation.

Using the $1^{st}$ derivative estimates for a predefined set of excitation/emission pair that are specific to the Gram family classification result, calculate the distance, $$d_a = [(m-m_a)^t \Sigma^{-1}(m-m_a)]^{1/2}$$

for each organism species defined in the model,
where
- a=1, 2, . . . , k, represents the number of organism species defined in the model
- $E^{-1}$ represents the inverse of the covariance matrix for the predefined set of excitation/emission pairs (same remark as before)
- m represents the vector of calculated values of the $1^{st}$ derivative, $m_{ij}$, of the natural log transform for each excitation/emission pair i, j
- $m_a$ represent the vector of mean values $m_{a(ij)}$ from a distribution for each class a at excitation/emission pair i, j
- t represent the transpose of the vector
- $(m-m_a)$ represent the vector of differences $m_{ij}-m_{a(ij)}$ for each excitation/emission pair i, j Step 5132 Gram family species classification interpretation.

Let $u_s$ represent the maximum distance threshold.
If all distances, $d_1, d_2, \ldots, d_a$, are greater than $u_t$, the classification result is Unknown.
Else, determine the value of $d_{min}$, the minimum value of $d_1, d_2, \ldots, d_a$
Let $w_s$ represent the low discrimination threshold factor.
If more than one distance, $d_1, d_2, \ldots, d_a$, is less than $(d_{min}*w_s)$, the classification result is Low Discrimination between the organism species having distances less than $(d_{min}*w_s)$
If only one distance, $d_1, d_2, \ldots, d_a$, is less than $(d_{min}*w_t)$, the classification result is the corresponding species.

Step 5134 Gram family species classification result.

If the Gram family species classification result is Unknown, the test organism classification is finalized at the Gram and family level.

If the Gram family species classification result is Low Discrimination, the test organism classification is finalized as the Gram, family, and species included in the low discrimination.

If the Gram family species classification result a single species, the test organism classification is finalized at the Gram, family, and species level.

At step 5136, the results determined at steps 5134, 5118, and 5126 are returned and reported to the user, e.g., on a user interface for the identification instrument, transmitted to an attached workstation, returned to another software module, or otherwise generated for the user.

Figure 9:
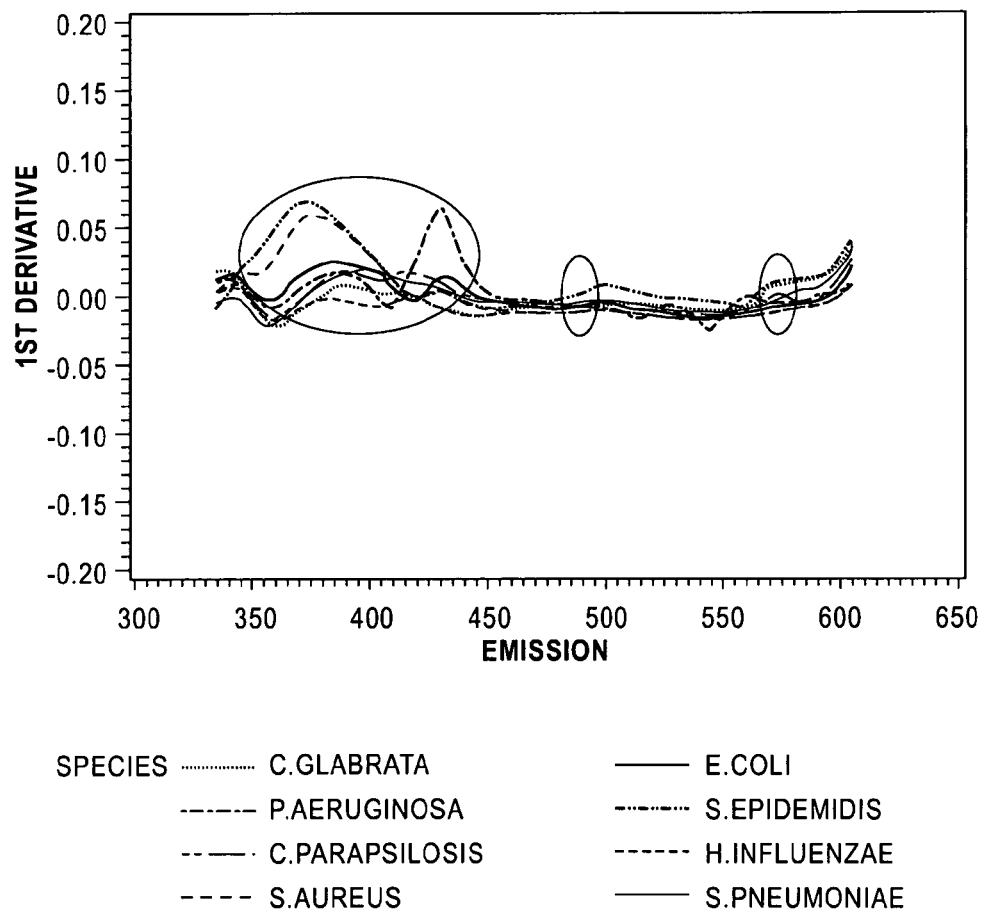

In regards to organism identification (step 5134), discrimination between species is possible only if the values of the first derivative (of the natural logarithm transform of the emission value) are unique for each species in the model at some portion of the emission range for at least one excitation wavelength. FIGS. 9 and 10 illustrate the discrimination potential between a subset of species for excitation wavelengths 315 nm (FIG. 9) and 415 nm (FIG. 10). Referring to FIG. 9, it is apparent that several of the species can be discriminated from the others based on the first derivative at excitation wavelength 315. The mathematical model uses the first derivative values (of natural log transform) for emissions where visual differences exist as inputs to discriminate between species. Using selected sections of values across the emission range the following species can be clearly discriminated from the others: *E. coli*, *H. influenzae*, *P. aeruginosa*, and *S. pneumoniae*. In addition, *S. aureus* and *S. epidermidis* can be discriminated from other species but not each other. The sections of values across the emission range at a given excitation wavelength are the predefined pairs in the inverse matrices $\Sigma^{-1}$ in the distance calculations in the processing steps described above. These pairs may for example be excitation at 315 nm and the range of emission values indicated by the circles shown in FIG. 9, i.e., (315/300-450), (315, 485-500), (315/570-580).

Referring to FIG. 10, it is apparent that the emissions at excitation wavelength 415 nm has the ability to discriminate between species. Using selected sections of values across the emission range *C. parasilopsis* and *P. auruginosa* can be clearly discriminated from the other species. It is also of interest to note the difference between first derivative values for *S. aureus* and *S. epidermidis* that occurs around emission 450 nm. When the information from the selected sections of values across the emission range for wavelengths 315 and 415 (FIGS. 9 and 10) is combined, all of the species in the model can be discriminated from each other at a high rate (>97% reliability).

To enhance fluorescence signals, microorganisms could either be coated with gold and/or silver nanoparticles prior to centrifugation/concentration, and/or the inner optical surface could be pre-coated with metal colloids of particular size and shape (refs: Lakowicz, *Anal. Biochem.* 337:171 (2005) for fluorescence; Efrima et al., *J. Phys. Chem. B.* (*Letter*) 102: 5947 (1998) for SERS). In another embodiment, the nanoparticles are present in a density cushion present in the separation device prior to centrifugation and associate with microorganisms as the microorganisms pass through the density cushion.

The taxonomic hierarchical classification method explained above in the context of FIGS. 2-10 is applicable to other data sets obtained from interrogation of a microbial agent. For example, the classification method would be equally useful in the case of that Raman scattering data or mass spectrometry data is obtained from a concentrated microbial agent instead of intrinsic fluorescence data. In the case of Raman scattering, data is obtained from known microbial agents and such data is analyzed (typically after transform steps are performed) to determined subsets of the data that are discriminatory between Gram, family and species and the results, i.e., discriminatory subsets stored. Similarly, data from an unknown microbial agent is subject to a transformation steps to minimize strain-to-strain variation between species; the transformation may be natural logarithm, first derivative, or other transform, the selection and details of the transformation will be within the ability of persons skilled in the art based upon examination of the data for known microbial agents. The processing of FIGS. 2A-2C (hierarchical classification at the Gram, Family and Species level) then proceeds. Alternatives to the minimum distance calculation used for classification, such as the well-known K-Nearest Neighbor classification algorithm, may be used for classification of the test sample at each hierarchical level. It will also be apparent that additional pre-processing steps may be required which are not shown in the flow chart of FIGS. 2A-2C, that are unique to the analytic test method, such as background subtraction or normalization, but these steps are known in the art and therefore a detailed description is not necessary.

Generalizing the foregoing, we have described a method for rapid identification and/or characterization of a microbial agent present in a sample, comprising the steps of: obtaining analytic test data of the microbial agent; transforming the analytic test data, thereby minimizing strain to strain variations in analytic test data within an organism group; and with the aid of a programmed computer, performing a multi-level classification algorithm coded as a set of processing instructions operating on the transformed analytic test data, the multiple levels corresponding to different levels in a taxonomic hierarchy for microbial agents suspected of being in the sample. In some embodiments the analytic test data (e.g., intrinsic fluorescence, Raman scattering) is performed while the microbial agent is concentrated within a test device in which the agent was separated and concentrated, as shown in FIG. 1; in other embodiments the concentrated agent is removed from the test device and subject to analysis is a separate instrument, e.g., mass spectrometer. Further examples of analytical methods which may be used are disclosed in U.S. Pat. No. 6,780,602, the content of which is incorporated by reference herein.

While an embodiment has been disclosed in which the sample is human or animal blood, obviously the invention is applicable to samples generally, which may be clinical or non-clinical samples. The methods could also be used to, identify microbial colonies removed from a plate or other form of microbial culture device, and in this situation, again, the sample from which such colonies are grown could be clinical or non-clinical samples, and thus not necessarily blood. For example, the sample can be a clinical or non-clinical sample suspected of containing one or more microbial agents. Clinical samples, such as a bodily fluid, include, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. Non-clinical samples that may be tested include, but are not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like.

Variation from the specifics from the disclosed embodiments are of course possible without departure from the scope of the invention. All questions' concerning scope are to be answered by reference to the appended claims.

We claim:

1. A method for rapid identification and/or characterization of a microbial agent present in a sample, comprising the steps of:
    obtaining fluorescence values over a range of emission wavelengths from the microbial agent, the range of emission wavelengths obtained at a plurality of excitation wavelengths;
    transforming the fluorescence measurements, thereby minimizing strain to strain variations in fluorescence measurements within an organism group, wherein transforming comprises computing a natural logarithm of the fluorescence values across a given excitation wavelength and calculating a first derivative of the natural logarithm values; and
    with the aid of a programmed computer, performing a multi-level classification algorithm coded as a set of processing instructions operating on the transformed fluorescence measurements, the multiple levels corresponding to different levels in a taxonomic hierarchy for microbial agents suspected of being in the sample.

2. The method of claim 1, wherein the multi-level classification algorithm proceeds monotonically in an order from a higher level in the taxonomic hierarchy to a lower level in the taxonomic hierarchy.

3. The method of claim 2, wherein the multilevel classification algorithm first classifies the microbial agent by Gram class, then family, and then species.

4. The method of claim 1, wherein the multi-level classification algorithm comprises, for each level in the algorithm, steps of:
    performing a distance calculation on transformed fluorescence values and an inverse of a covariance matrix for a pre-defined set of excitation/emission pairs;
    performing a classification interpretation using the results of the distance calculation and a minimum distance threshold and a low discrimination threshold; and
    generating a classification result.

5. The method of claim 4, wherein the algorithm includes a Gram classification level set of processing instructions, and
    wherein the Gram classification level includes a first branch of processing instructions including a distance calculation for each Gram class defined in a model comprising a set of microbial agents suspected of being in the sample and a Gram classification interpretation step;
    wherein the Gram classification includes a second branch of processing instructions including a distance calculation for all organism families defined in the model and an all families classification interpretation step; and
    wherein the step of generating a classification result includes a step of pooling results from the Gram classification interpretation and all families classification interpretation.

6. The method of claim 4, wherein the algorithm includes a Gram-family classification level including processing instructions performing a distance calculation for each organism family defined in a model comprising a set of microbial agents suspected of being in the sample and a Gram-family classification interpretation step using the results of the distance calculation for each organism family defined in a model, a minimum distance threshold and a low discrimination threshold.

7. The method of claim 4, wherein the algorithm includes a Gram-family species classification level including processing instructions performing a distance calculation for each organism species defined in a model comprising a set of microbial agents suspected of being in the sample and a Gram-family species classification interpretation step using the results of the distance calculation for each organism family defined in a model, a minimum distance threshold and a low discrimination threshold.

8. The method of claim 4, wherein the pre-defined set of excitation/emission pairs are obtained from intrinsic fluorescence measurements from known microbial agents across a range of excitation and emission values, the pre-defined set of excitation/emission pairs selected for their ability to distinguish between different microbial agents.

9. A method for identification and/or characterization of a microbial agent present in a sample, comprising the steps of:
    experimentally obtaining intrinsic fluorescence measurements from known microbial agents across a range of excitation and emission values and selecting from such measurements a set of excitation/emission pairs for their ability to distinguish between different microbial agents;

obtaining intrinsic fluorescence measurements from an unknown microbial agent at the set of excitation/emission pairs;

transforming the intrinsic fluorescence measurements from an unknown microbial agent thereby minimizing strain to strain variations in intrinsic fluorescence measurements within an organism group, wherein transforming comprises computing a natural logarithm of the fluorescence values across a given excitation wavelength and calculating a first derivative of the natural logarithm values; and identifying and/or characterizing the unknown microbial agent using the transformed intrinsic fluorescence measurements and the experimentally obtained intrinsic fluorescence measurements from known microbial agents with the aid of a programmed computer executing a classification algorithm, wherein the classification algorithm comprises a multi-level classification algorithm coded as a set of processing instructions operating on the transformed intrinsic fluorescence measurements, the multiple levels corresponding to different levels in a taxonomic hierarchy for microbial agents suspected of being in the sample.

10. The method of claim 1, wherein the sample comprises a sample of human or animal blood.

11. The method of claim 1, wherein the microbial agent is concentrated into pellet or pellet-like mass and wherein the fluorescence measurements are obtained from the pellet or pellet-like mass.

12. The method of claim 11, wherein the pellet or pellet-like mass is contained within sealed disposable device.

13. The method of claim 9, wherein the sample comprises a sample of human or animal blood.

14. The method of claim 9, wherein the unknown microbial agent is concentrated into pellet or pellet-like mass and wherein the intrinsic measurements of the unknown microbial agent are obtained from the pellet or pellet-like mass.

15. The method of claim 14, wherein the pellet or pellet-like mass is contained within sealed disposable device.

16. A computer having a memory storing instructions for performing the method of claim 1.

17. The method of claim 11, wherein the fluorescence measurements are intrinsic fluorescence measurements.

18. The method of claim 17, further comprising obtaining the intrinsic fluorescence measurements by using front-face mode interrogation of the pellet or pellet-like mass.

* * * * *